US009956170B2

(12) United States Patent
Cantor et al.

(10) Patent No.: US 9,956,170 B2
(45) Date of Patent: *May 1, 2018

(54) DRY POWDER PHARMACEUTICAL COMPOSITIONS FOR PULMONARY ADMINISTRATION, AND METHODS OF MANUFACTURING THEREOF

(75) Inventors: Adam S. Cantor, River Falls, WI (US); Jacqueline M. Ganser, Falcon Heights, MN (US); Michael W. Mueting, Stillwater, MN (US); Stephen W. Stein, Lino Lakes, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 694 days.

This patent is subject to a terminal disclaimer.

(21) Appl. No.: 12/995,319

(22) PCT Filed: Jun. 22, 2009

(86) PCT No.: PCT/US2009/048096
§ 371 (c)(1),
(2), (4) Date: Nov. 30, 2010

(87) PCT Pub. No.: WO2009/158300
PCT Pub. Date: Dec. 30, 2009

(65) Prior Publication Data
US 2011/0076336 A1    Mar. 31, 2011

Related U.S. Application Data

(60) Provisional application No. 61/075,942, filed on Jun. 26, 2008.

(51) Int. Cl.
| A61K 9/14 | (2006.01) |
| A61K 31/56 | (2006.01) |
| A61K 31/58 | (2006.01) |
| A61P 11/06 | (2006.01) |
| A61P 29/00 | (2006.01) |
| A61K 9/00 | (2006.01) |
| A61K 31/00 | (2006.01) |

(52) U.S. Cl.
CPC ............ *A61K 9/0075* (2013.01); *A61K 31/00* (2013.01); *A61K 31/58* (2013.01)

(58) Field of Classification Search
CPC ....... A61K 31/00; A61K 31/58; A61K 9/0075
See application file for complete search history.

(56) References Cited

U.S. PATENT DOCUMENTS

| 2,801,185 A | 7/1957 | Iler |
| 4,455,205 A | 6/1984 | Olson et al. |
| 4,478,876 A | 10/1984 | Chung |
| 4,486,504 A | 10/1984 | Chung |
| 4,491,508 A | 1/1985 | Olson et al. |
| 4,522,958 A | 6/1985 | Das et al. |
| 5,037,579 A | 8/1991 | Matchett |
| 5,258,225 A | 11/1993 | Katsamberis |
| 5,443,603 A | 8/1995 | Kirkendall |
| 6,051,252 A | 4/2000 | Liebowitz et al. |
| 6,153,224 A | 11/2000 | Staniforth |
| 6,329,058 B1 | 12/2001 | Arney et al. |
| 6,432,526 B1 | 8/2002 | Arney et al. |
| 6,811,096 B2 | 11/2004 | Frazier et al. |
| 6,811,767 B1* | 11/2004 | Bosch et al. ..................... 424/45 |
| 7,189,768 B2 | 3/2007 | Baran, Jr. et al. |
| 2003/0102099 A1* | 6/2003 | Yadav et al. .................. 162/208 |
| 2005/0113489 A1 | 5/2005 | Baran, Jr. et al. |
| 2005/0196345 A1 | 9/2005 | Diederichs et al. |
| 2005/0238804 A1 | 10/2005 | Garbar et al. |
| 2007/0212542 A1 | 9/2007 | Guo et al. |
| 2010/0266697 A1 | 10/2010 | Dunbar |

FOREIGN PATENT DOCUMENTS

| WO | WO 02/00197 | 1/2002 |
| WO | WO 02/43700 | 6/2002 |
| WO | WO 2007/019229 | 2/2007 |
| WO | WO 2007/117661 | 10/2007 |
| WO | WO 2008/002568 | 1/2008 |
| WO | WO 2009/142852 | 11/2009 |

OTHER PUBLICATIONS

Linsenbuhler, M,, et al., "An innovative dry powder coating process in non-polar liquids producing tailor-made miro-particles," *Powder Technology*, 158, 2003, pp. 3-20.
Kawashima, Y., et al., Design of inhalation dry powder of pranlukast hydrate to improve dispersibility by the surface modification with light anhydrous silicic acid (AEROSIL 200), *Int'l Journal of Pharmaceutics*, 173: 1998, pp. 243-251.
Li, J. et al., "Visualization and Characterization of Poly(amidoamine) Dendrimers by Atomic Force Microscopy," *Langmuir 2000*, 16, 5613-5616.
Sastre et al., "On the Incorporation of Buckminsterfullerene $C_{60}$ in the Supercages of Zeolite Y," *J. Phys. Chem.* B 1997, 101, 10184-10190.
Binks, B.P. et al., "Phase Inversion of particle-stabilized materials from foams to dry water," *Nature Materials*, vol. 5, Nov. 2006, 865-869.
Ben-Jebria, et al.; "Inhalation System for Pulmonary Aerosol Drug Delivery in Rodents Using Large Porous Particles"; Aerosol Science and Technology; vol. 32, No. 5; 2000; pp. 421-433.

\* cited by examiner

*Primary Examiner* — Matthew P Coughlin
*Assistant Examiner* — Thurman M Wheeler

(57) ABSTRACT

A method of making a dry powder pharmaceutical composition comprising: providing inactive ingredient particles; providing a micronized active ingredient; mixing the inactive ingredient particles with surface-modified nanoparticles to provide an inactive ingredient comprised of particles having surfaces with the surface-modified nanoparticles deposited on the surfaces; and/or mixing the micronized active ingredient with surface-modified nanoparticles to provide a micronized active ingredient comprised of particles having surfaces with the surface-modified nanoparticles deposited on the surfaces; and then mixing the micronized active ingredient with the inactive ingredient; the dry powder compositions made by the method; a use of said composition for the manufacture of a medicament for being delivered to the lungs of a mammal by administering a therapeutic amount of the dry powder pharmaceutical composition, and a dry powder inhalation device comprising a mouth piece, a powder containment system, and the dry powder pharmaceutical composition are disclosed.

15 Claims, No Drawings

DRY POWDER PHARMACEUTICAL COMPOSITIONS FOR PULMONARY ADMINISTRATION, AND METHODS OF MANUFACTURING THEREOF

CROSS REFERENCE TO RELATED APPLICATIONS

This application is a national stage filing under 35 U.S.C. 371 of PCT/US2009/048096, filed Jun. 22, 2009, which claims priority to U.S. Provisional Application No. 61/075,942, filed Jun. 26, 2008, the disclosure of which is incorporated by reference in its/their entirety herein.

BACKGROUND

The preparation or delivery of pharmaceutical drugs and medicaments as powders is demanding. Pharmaceutical applications must take careful account of various particle or powder characteristics, and pharmaceutical compositions often are prepared as powders as an intermediate step to final formulation in many forms for delivery to the patient. Pharmaceutical compositions can be tableted or encapsulated for oral gastro-intestinal ingestion and delivery. Powder pharmaceutical compositions also can be incorporated into a dry powder inhaler (DPI) for delivery to the respiratory tract. Dry powder inhalation of a pharmaceutical composition requires unique and challenging physical property profiles for a powder. For efficient and efficacious delivery to the lung in powder form, drug particles must be sufficiently small and deagglomerated. Lung deposition improves substantially for particles less than 5 microns in aerodynamic diameter and decreases substantially for particles with an aerodynamic diameter greater than 5 microns. However, below 5 microns in particle diameter, deagglomeration efficiency declines markedly.

Balancing these competing effects, in one example, has involved adsorbing small respirable drug particles onto larger inert carrier particles which provide for bulk deagglomeration but which require additional energy to release the drug from the surface of the carrier particles. Recent advances in improving the flowability characteristics of powders by adding surface-modified nanoparticles are disclosed in International Publication No. WO 2007/019229, entitled "Compositions Exhibiting Improved Flowability" (incorporated herein by reference).

There is a continuing need for compositions and methods that provide for more efficient and efficacious delivery of pharmaceutical compositions in powder form.

SUMMARY

It has now been found that delivery efficiency of an active ingredient in a dry powder pharmaceutical composition containing both the active ingredient and an inactive ingredient can be increased by treating either or both ingredients separately with surface-modified nanoparticles. The active and inactive ingredients are then combined to provide a dry powder composition. For certain embodiments, a relatively large proportion of the composition can comprise the inactive ingredient, thereby allowing delivery of a small amount of drug, while delivering an amount of composition which can be reproducibly metered. Such compositions can be used in a dry powder inhaler to deliver the active ingredient to the lung of a mammal.

Accordingly, in one embodiment, there is provided a method of making a dry powder pharmaceutical composition comprising:
 providing inactive ingredient particles;
 providing a micronized active ingredient;
 mixing the inactive ingredient particles with surface-modified nanoparticles to provide an inactive ingredient comprised of particles having surfaces with the surface-modified nanoparticles deposited on the surfaces; and/or mixing the micronized active ingredient with surface-modified nanoparticles to provide a micronized active ingredient comprised of particles having surfaces with the surface-modified nanoparticles deposited on the surfaces; and
 then mixing the micronized active ingredient with the inactive ingredient.

The surface-modified nanoparticles may have a hydrophilic or hydrophobic surface modification. Examples of core materials for the nanoparticles include silicas, titania, iron oxides, zinc oxides, alumina, metal phosphates such as a calcium phosphate, metal sulfates, metal chlorides, and combinations thereof. For certain embodiments, the mean diameter of the nanoparticles may be 20 nm or less.

The particles of the powder drug composition in certain embodiments have a median particle size diameter less than 200 micrometers. The diameter of these particles, however, is substantially larger than the diameter of the nanoparticles, for example, 10 to 1000 times larger.

In another embodiment, there is provided a dry powder pharmaceutical composition comprising:
 an inactive ingredient comprised of particles;
 a micronized active ingredient; and
 surface-modified nanoparticles;
 wherein the composition is made by a process comprising:
  providing inactive ingredient particles;
  mixing the inactive ingredient particles with the surface-modified nanoparticles to provide an inactive ingredient comprised of particles having surfaces with the surface-modified nanoparticles deposited on the surfaces; and/or mixing the micronized active ingredient with the surface-modified nanoparticles to provide a micronized active ingredient comprised of particles having surfaces with the surface-modified nanoparticles deposited on the surfaces; and
  then mixing the micronized active ingredient with the inactive ingredient.

In another embodiment, there is provided a method of delivering medicament to the lungs of a mammal by administering a therapeutic amount of a dry powder pharmaceutical composition, the composition comprising:
 an inactive ingredient comprised of particles;
 a micronized active ingredient; and
 surface-modified nanoparticles;
 wherein the composition is made by a process comprising:
  providing inactive ingredient particles;
  mixing the inactive ingredient particles with the surface-modified nanoparticles to provide an inactive ingredient comprised of particles having surfaces with the surface-modified nanoparticles deposited on the surfaces; and/or mixing the micronized active ingredient with the surface-modified nanoparticles to provide a micronized active ingredient comprised of particles having surfaces with the surface-modified nanoparticles deposited on the surfaces; and
  then mixing the micronized active ingredient with the inactive ingredient.

In another embodiment, there is provided a dry powder inhalation device comprising a mouth piece, a powder containment system, and a dry powder pharmaceutical composition, the composition comprising:
- an inactive ingredient comprised of particles;
- a micronized active ingredient; and
- surface-modified nanoparticles;

wherein the composition is made by a process comprising:
- providing inactive ingredient particles;
- mixing the inactive ingredient particles with the surface-modified nanoparticles to provide an inactive ingredient comprised of particles having surfaces with the surface-modified nanoparticles deposited on the surfaces; and/or mixing the micronized active ingredient with the surface-modified nanoparticles to provide a micronized active ingredient comprised of particles having surfaces with the surface-modified nanoparticles deposited on the surfaces; and then mixing the micronized active ingredient with the inactive ingredient.

Definitions

The term "nanoparticle" as used herein refers to particles, groups of particles, particulate molecules (i.e., small individual groups or loosely associated groups of molecules) and groups of particulate molecules that while potentially varied in specific geometric shape have an effective, average, or mean diameter of less than 100 nanometers.

The term "mean" as applied herein to a diameter, in certain embodiments, preferably is mass mean. For example, mean physical diameter as used herein, in certain embodiments, preferably is mass mean physical diameter.

The term "comprising" and variations thereof (e.g., comprises, includes, etc.) do not have a limiting meaning where these terms appear in the description and claims.

As used herein, "a," "an," "the," "at least one," and "one or more" are used interchangeably, unless the context clearly dictates otherwise.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the present specification and attached claims are approximations that can vary depending upon the desired properties sought to be obtained by those skilled in the art utilizing the teachings disclosed herein.

Also herein, the recitation of numerical ranges by endpoints includes all numbers subsumed within that range (e.g. 1 to 5 includes 1, 1.5, 2, 2.75, 3, 3.80, 4, and 5; between 1 and 5 includes 1.1, 1.5, 2, 2.75, 3, 3.80, 4, and 4.5) and any range within that range.

The above summary of the present invention is not intended to describe each disclosed embodiment or every implementation of the present invention. The description that follows more particularly exemplifies illustrative embodiments.

DETAILED DESCRIPTION OF ILLUSTRATIVE EMBODIMENTS

Unexpectedly, Applicants have found that, in a dry powder pharmaceutical composition containing both an active ingredient and an inactive ingredient which can be present as a carrier or bulking agent, by treating either the active or inactive ingredient or both ingredients separately with surface-modified nanoparticles, an increase in delivery efficiency, respirable fraction, or both may be obtained. After the treatment with the surface modified nanoparticles, the active and inactive ingredients are combined to provide the dry powder composition.

For certain embodiments, a relatively large proportion of the composition can comprise the inactive ingredient, thereby allowing delivery of a small amount of drug, while delivering an amount of composition which can be reproducibly metered to minimize variability between doses. In addition, certain manufacturing limitations, for example, the inability to accurately fill blisters or capsules (or other single dose containers) with doses of powder less than about 1 mg, are overcome by using larger powder doses of the present compositions. For certain embodiments, the powder dose is 2 to 20 mg. For certain of these embodiments, the powder dose is 2 to 10 mg.

Compositions described herein can be used in a dry powder inhaler to deliver the active ingredient to the lung of a mammal. For certain embodiments, preferably the respirable fraction of the composition is increased by at least 20 percent using the present compositions as compared with the same compositions except without the nanoparticles or as compared with the same composition except that the nanoparticles are combined with the active and inactive ingredients at the same time, that is when the active and inactive ingredients are already combined. For certain of these embodiments, the respirable fraction is increased by at least 30 percent. For certain of these embodiments, the respirable fraction is increased by at least 50 percent or by at least 75 percent.

For certain embodiments, including any one of the above embodiments, preferably active ingredient delivery efficiency is increased by at least 10 percent using the present compositions as compared with the same compositions except without the nanoparticles or as compared with the same composition except that the nanoparticles are combined with the active and inactive ingredients at the same time, that is when the active and inactive ingredients are already combined. For certain of these embodiments, the delivery efficiency is increased by at least 20 percent. For certain of these embodiments, the delivery efficiency is increased by at least 50 percent.

Dry powder pharmaceutical compositions described herein are made by a method comprising providing inactive ingredient particles; providing a micronized active ingredient; mixing the inactive ingredient particles with surface-modified nanoparticles to provide an inactive ingredient comprised of particles having surfaces with the surface-modified nanoparticles deposited on the surfaces; and/or mixing the micronized active ingredient with surface-modified nanoparticles to provide a micronized active ingredient comprised of particles having surfaces with the surface-modified nanoparticles deposited on the surfaces; and then mixing the micronized active ingredient with the inactive ingredient. It is believed that when either ingredient, but not the other, is treated with the surface-modified nanoparticles, after mixing the ingredients, some portion of the nanoparticles associated with the treated ingredient become associated with the surface of the ingredient not previously treated with the nanoparticles. For certain of these embodiments, preferably the method comprises mixing the inactive ingredient particles with surface-modified nanoparticles to provide an inactive ingredient comprised of particles having surfaces with the surface-modified nanoparticles deposited on the surfaces; and then mixing the micronized active ingredient with the inactive ingredient. For certain of these embodiments, the method further comprises mixing the micronized active ingredient with surface-modified nanoparticles prior to mixing the micronized active ingredient with the inactive ingredient.

For certain embodiments, including any one of the above methods, the method further comprises dry blending inactive ingredient particles without surface-modified nanoparticles with the inactive ingredient comprised of particles having surfaces with the surface-modified nanoparticles deposited on the surfaces, wherein the dry blending is carried out prior to mixing the micronized active ingredient with the inactive ingredient. A variety of compositions with various amounts of inactive ingredient, or various combinations of inactive ingredient can thereby be conveniently provided at a lower cost, using a single batch of inactive ingredient (or combination of inactive ingredients) treated with surface-modified nanoparticles.

When mixing the inactive ingredient particles or the micronized active ingredient with the surface-modified nanoparticles in any of the above methods, any suitable, conventional mixing or blending process can be used as long as the nanoparticles are dispersed to the extent that the nanoparticles are not aggregated or, if aggregated, the average diameter of the aggregated particles is less than 100 nm or within any one of the ranges stated herein for the nanoparticles. For certain embodiments, including any one of the above embodiments, mixing the micronized active ingredient with the surface-modified nanoparticles is carried out in a liquid, and then the liquid is removed. For certain of these embodiments, the micronized active ingredient is substantially insoluble in the liquid, and the surface-modified nanoparticles are dispersible in the liquid. For certain embodiments, including any one of the above embodiments, mixing the inactive ingredient particles with the surface-modified nanoparticles is carried out in a liquid, and then the liquid is removed to provide the inactive ingredient comprised of particles having surfaces with the surface-modified nanoparticles deposited on the surfaces; and wherein the inactive ingredient particles are substantially insoluble in the liquid, and the surface-modified nanoparticles are dispersible in the liquid.

The mixing can be carried out by dispersing the surface-modified nanoparticles in the liquid, adding the inactive ingredient particles or instead adding the micronized active ingredient, mixing, and removing the liquid. The liquid can be hydrophilic or hydrophobic. When the surface-modified nanoparticles have a hydrophilic surface, the liquid is preferably hydrophilic, for example, the liquid can be water, ethanol, isopropanol, combinations thereof, and the like. When the nanoparticle surface is hydrophobic, the liquid is preferably hydrophobic, for example the liquid can be heptane, hexane, octane, toluene, combinations thereof, or the like.

The liquid can be removed by known processes while avoiding excessive heat that could degrade the active ingredient or cause melting or dissolving of any of the ingredients. For certain embodiments, including any one of the above embodiments where the liquid is removed, the liquid is removed by spray drying, rotary evaporation, bulk evaporation, or freeze drying.

Other methods of mixing the inactive ingredient particles or the micronized active ingredient with the surface-modified nanoparticles may be used. For example, the mixing may be carried out by blending the nanoparticles with either of the ingredients as powders, i.e., dry blending. In another example, the surface-modified nanoparticles may be dispersed in a liquid as described above, and the resulting dispersion sprayed onto the inactive ingredient particles or onto the micronized active ingredient followed by quickly removing the liquid, for example, by evaporation. Such methods are described in International Application No. PCT/US2009/040892.

For certain embodiments, including any one of the above embodiments, mixing the active ingredient with the inactive ingredient is carried out by dry blending. Known dry blending processes may be used. However, excessive heat that could degrade the active ingredient or cause melting of any of the ingredients is avoided. Suitable methods include shaking, roll mixing, stirring, tumble mixing, and the like.

As indicated above, the dry powder pharmaceutical compositions described herein are comprised of an inactive ingredient comprised of particles; a micronized active ingredient; and surface-modified nanoparticles; and the compositions are prepared as described in any one of the above methods. For certain of these embodiments, the composition comprises the inactive ingredient comprised of particles having surfaces with the surface-modified nanoparticles deposited on the surfaces; and the micronized active ingredient; wherein the composition is made by a process comprising providing inactive ingredient particles; mixing the inactive ingredient particles with the surface-modified nanoparticles to provide the inactive ingredient comprised of particles having surfaces with the surface-modified nanoparticles deposited on the surfaces; and then mixing the micronized active ingredient with the inactive ingredient.

In another embodiment, there is provided a method of delivering medicament to the lungs of a mammal by administering a therapeutic amount of a dry powder pharmaceutical composition. The composition is any one of the compositions described above.

In another embodiment, there is provided a dry powder inhalation device comprising a mouth piece, a powder containment system, and a dry powder pharmaceutical composition. The composition is any one of the compositions described above, and the composition may be placed in the containment system. Suitable dry powder inhalation devices may contain either a single dose or multiple doses. Multiple doses may be stored in a reservoir or in multiple, individually packaged doses stored in, for example, blisters or capsules. Examples of suitable devices include, but are not limited to, the TURBUHALER (Astra Zeneca), CLICK-HALER (Innovata Biomed), EASYHALER (Orion), ACCUHALER, DISKUS, DISKHALER, ROTAHALER (GlaxoSmithKline), HANDIHALER, INHALATOR, AEROHALER (Boehringer Ingelheim), AEROLIZER (Schering Plough), and NOVOLIZER (ASTA Medica).

The inactive ingredient is comprised of particles having a mean physical diameter of less than 1,000 microns. Mean physical diameter can be measured by known methods, for example, by laser diffraction or microscopy. The particle size of the inactive ingredient is selected to provide a well-mixed powder composition that is stable from segregation and achieves sufficient deagglomeration from the active ingredient during powder delivery to maximize the respirability of the active ingredient. For certain embodiments, including any one of the above embodiments, preferably the inactive ingredient is comprised of particles having a mean physical diameter of less than 200 micrometers. In certain embodiments, the mean physical diameter is selected so as to reduce interparticle adhesion and, thus, reduce the potential for particle agglomeration, thereby improving the flowability of the powder composition and the ability to easily and uniformly blend the inactive ingredient powder with an active ingredient. For certain of these embodiments, the mean physical diameter is at least 10 micrometers or at least 20 micrometers. In certain embodiments the mean physical diameter is selected so as to minimize the likelihood that a blend of inactive ingredient and active ingredient would separate from each other due to differing mean particle sizes. For certain of these embodiments, the mean physical diameter is less than 100 micrometers or less than 60 micrometers. For certain of these embodiments, the mean physical diameter is between 10 and 60 micrometers. For certain of these embodiments, the mean physical diameter is between 20 and 60 micrometers.

The micronized active ingredient is comprised of particles having a mean physical diameter no greater than 100 micrometers. For certain embodiments, including any one of the above embodiments, preferably the active ingredient is comprised of particles having a mean physical diameter of less than 10 micrometers, more preferably less than 5 micrometers. In certain embodiments, the particles may have a mean physical diameter of between about 1 and 5 micrometers. In one embodiment, the micronized active ingredient may be formed by processes, such as milling, grinding, and high-pressure homogenization, that cause an overall reduction in particle size of larger active ingredient particles. In another embodiment, the micronized active ingredient may, for example, be formed by processes, such as recrystallization, lyophilization, and spray drying, that lead directly to formation of particles of an appropriate particle size. In still another embodiment, the micronized active ingredient may result from controlled agglomeration or aggregation of smaller active ingredient particles. It should be understood that the term "micronized" is used to refer to relatively small particles of the sizes described above and does not suggest that these particles are prepared by any particular process.

The mean aerodynamic diameter of the micronized active ingredient particles is typically no greater than 100 micrometers. Mean aerodynamic diameter can be measured by known methods, for example, by laser time of flight or by cascade impactor testing. For certain embodiments, the particles have a mean aerodynamic diameter which permits the active ingredient to be deposited in the lower lung. For certain embodiments, including any one of the above embodiments, preferably the active ingredient is comprised of particles having a mean aerodynamic diameter of less than 10 micrometers, more preferably less than 5 micrometers. In certain embodiments, the particles may have a mean aerodynamic diameter of between about 1 and 5 micrometers.

In certain embodiments, the particles comprising the inactive ingredient are sufficiently larger than the particles comprising the active ingredient so that when a patient inhales the dry powder composition a substantial portion of the respirable active ingredient particles deposit in the patient's lung, whereas the larger inactive ingredient particles and the nanoparticles on the surface of the inactive ingredient particles collect in the patient's mouth and throat. For certain embodiments, including any one of the above embodiments, the mean physical diameter of the particles comprising the inactive ingredient is at least 10 fold greater than the mean aerodynamic diameter of the particles comprising the active ingredient.

As indicated above, a relatively large portion of the composition is comprised of the inactive ingredient to obviate problems associated with delivering small doses of pure or essentially pure drug. For certain embodiments, including any one of the above embodiments, preferably the active ingredient and the inactive ingredient are each present in an amount such that the weight ratio of the amount of active ingredient to the amount of the inactive ingredient is not more than 1:3. For certain of these embodiments, the weight ratio is not more than 1:9. For certain of these embodiments, the weight ratio is not more than 5:95 or 1:99. For certain of these embodiments, the weight ratio is 1:9 to 0.01:99.99 and sometimes 1:99 to 0.1:99.9.

The dry powder pharmaceutical compositions described herein include a blend of one or more active ingredients, which are drugs or medicaments, with one or more inactive ingredients, which include excipients or carriers. Suitable excipients are listed in the Handbook of Pharmaceutical Excipients (Rowe, et al., APhA Publications, 2003), examples of which include microcrystalline cellulose, dicalcium phosphate, lactose (including lactose monohydrate), trehalose, sucrose, mannose, mannitol, sorbitol, calcium carbonate, starches, and magnesium or zinc stearates. For certain embodiments, including any one of the above embodiments, the inactive ingredient is selected from the group consisting of lactose, trehalose, sucrose, mannitol, or a combination thereof.

The active ingredient of the present compositions can be used for the diagnosis, treatment, cure, prevention, or mitigation of disease. Examples of such drugs include but are not limited to medicaments such as antiallergics, analgesics, bronchodilators, antihistamines, therapeutic proteins and peptides, antitussives, anticholinergics, anginal preparations, antibiotics, anti-inflammatory preparations, diuretics, hormones, or sulfonamides, such as, for example, a vasoconstrictive amine, an enzyme, an alkaloid or a steroid, salts thereof, solvates thereof, enantiomers thereof, and combinations of any one or more of these. For certain embodiments, including any one of the above embodiments, the active ingredient is selected from the group consisting of antiallergics, antiasthmatics, antiinflammatories, bronchodilators, steroids, anticholinergics, salts thereof, solvates thereof, enantiomers thereof, and a combination thereof.

Specific examples of medicaments include isoproterenol, phenylephrine, phenylpropanolamine, glucagon, adrenochrome, trypsin, epinephrine, ephedrine, narcotine, codeine, atropine, heparin, morphine, dihydromorphinone, dihydromorphine, ergotamine, scopolamine, methapyrilene, cyanocobalamin, terbutaline, rimiterol, salbutamol (albuterol), isoprenaline, fenoterol, oxitropium, tiotropium, reproterol, budesonide, flunisolide, ciclesonide, formoterol, fluticasone propionate, salmeterol, procaterol, ipratropium, triamcinolone acetonide, tipredane, mometasone furoate, colchicine, pirbuterol, beclomethasone, beclomethasone dipropionate, orciprenaline, fentanyl, diamorphine, and dilitiazem. Other examples include antibiotics, such as neomycin, cephalosporins, streptomycin, penicillin, procaine penicillin, tetracycline, chlorotetracycline, hydroxytetracycline; adrenocorticotropic hormone and adrenocortical hormones, such as cortisone, hydrocortisone, hydrocortisone acetate and prednisolone; antiallergy compounds such as cromolyn sodium and nedocromil; protein and peptide molecules such as insulin, pentamidine, calcitonin, amiloride, interferon, LHRH analogues, IDNAase, heparin, and others.

For certain embodiments, including any one of the above embodiments, the active ingredient is selected from the group consisting of budesonide, albuterol, formoterol, fluticasone, salmeterol, mometasone, tiotropium, beclomethasone, salts thereof, solvates thereof, enantiomers thereof, and a combination thereof.

For a specific application the drug or medicaments may be used as either a free base or as one or more salts thereof. The choice of a free base or salt will be influenced by the biological impact as well as the chemical and physical stability (e.g., its tendency toward solvates, multiple polymorphs, friability, etc.) of the drug or medicament in a given formulation. Examples of anionic salts of drugs and medicaments that may be used in the present compositions include acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate (embonate), pantothenate, phosphatediphosphate, polygalacturonate, salicylate, stearate, subacetate, succinate, sulphate, tannate, tartrate, and triethiodide.

Examples of cationic salts of a drug or medicament that may be used in the present compositions include alkali metals, e.g., sodium and potassium; and ammonium salts and salts of amines known in the art to be pharmaceutically acceptable, e.g., glycine, ethylene diamine, choline, diethanolamine, triethanolamine, octadecylamine, diethylamine, triethylamine, 1-amino-2-propanol, 2-amino-2-(hydroxymethyl)propane-1,3-diol, and 1-(3,4-dihydroxyphenyl)-2-isopropylaminoethanol.

The surface-modified nanoparticles used in the present compositions are comprised of a core material and a surface that is different (i.e., modified) from the core material. The core material may be inorganic or organic and is selected such that it is compatible with the active ingredient and with the inactive ingredient and suitable for the application for which the dry powder composition is intended. The selection of the core material will also be governed at least in part by specific performance requirements for the composition. For example, the performance requirements for the composition might require that a given core material have certain dimensional characteristics (e.g., size and shape), compatibility with the surface modifying materials along with certain stability requirements (e.g., insolubility in a processing or mixing liquid, good dispersibility in a processing or mixing liquid). Requirements can include, for example, biocompatibility, biosolubility, biodegradability, and stability under more extreme environments (e.g., higher temperatures during processing or shipping, resistance to moisture uptake) as well as the ability to dry the surface-modified nanoparticles down to a powder and subsequently maintain the ability to re-disperse the nanoparticles in a processing or mixing liquid.

Suitable inorganic nanoparticle core materials include metal oxide nanoparticles such as silica, titania, alumina, iron oxide, zinc oxide, antimony oxide, tin oxide, alumina/silica, ceria, vanadia, metal phosphates, e.g., calcium phosphates including hydroxyapatite, metal sulfates, metal chlorides, and combinations thereof. For certain embodiments, including any one of the above embodiments, the surface-modified nanoparticles comprise a core, the core comprising an inorganic material selected from the group consisting of silica, titania, alumina, an oxide of zinc, an oxide of iron, metal phosphates, metal sulfates, metal chlorides, or a combination thereof. Metals such as gold, silver, or other precious metals can also be utilized as solid particles or as coatings on organic or inorganic particles.

Suitable organic nanoparticle core materials include, for example, organic polymeric nanospheres, sugars such as lactose, trehalose, glucose or sucrose, and aminoacids. For certain embodiments, including any one of the above embodiments except where the core material is inorganic, the surface-modified nanoparticles comprise a core, the core comprising an organic polymer. For certain of these embodiments, the core comprises polystyrene. Organic polymeric nanospheres are known and include nanospheres that comprise polystyrene, such as those available from Bangs Laboratories, Inc. of Fishers, Ind. as powders or dispersions. Such organic polymeric nanospheres will generally have average particle sizes ranging from 20 nm to not more than 60 nm.

A selected nanoparticle core material may be used alone or in combination with one or more other nanoparticle core materials including mixtures and combinations of organic and inorganic nanoparticle materials. Such combinations may be uniform or have distinct phases which can be dispersed or regionally specific, e.g., layered or of a core-shell type structure.

The nanoparticle core, whether inorganic or organic, and in whatever form employed, will have an mean particle diameter of less than 100 nm. For certain embodiments, the nanoparticles have a mean particle diameter of not more than 50 nm, preferably not more than 20 nm; in certain embodiments from 2 nm to 20 nm; and in certain other embodiments from 3 nm to 10 nm or more preferably from 4 nm to 8 nm. If the chosen nanoparticle or combination of nanoparticles are themselves aggregated, the maximum preferred cross-sectional dimension of the aggregated particles will be within any one of these stated ranges.

In an exemplary embodiment, another class of surface-modified organic nanoparticles includes buckminsterfullerenes (fullerenes), dendrimers, branched and hyperbranched "star" polymers such as 4, 6, or 8 armed polyethylene oxides (available, for example, from Aldrich Chemical Company of Milwaukee, Wis. or Shearwater Corporation of Huntsville, Ala.) whose surfaces have been chemically modified. Specific examples of fullerenes include $C_{60}$, $C_{70}$, $C_{82}$, and $C_{84}$. Specific examples of dendrimers include polyamidoamine (PAMAM) dendrimers of Generations 2 through 10 (G2-G10), available also from, for example, Aldrich Chemical Company of Milwaukee, Wis.

In many cases it may be desirable for the nanoparticles utilized in the invention to be substantially spherical in shape. In other applications, however, more elongated shapes may be desired. Aspect ratios of not more than 10 are preferred, with aspect ratios not more than 3 generally more preferred. The core material will substantially determine the final morphology of the particle and thus a significant influence in selection of the core material may be the ability to obtain a desired size and shape in the final particle.

The surface of the selected nanoparticle core material will generally be chemically or physically modified in some manner. Both direct modification of a core surface as well as modification of a permanent or temporary shell on a core material are envisioned. Such modifications may include, for example, covalent chemical bonding, hydrogen bonding, electrostatic attraction, London forces, and hydrophilic or hydrophobic interactions so long as the interaction is maintained at least during the time period required for the nanoparticles to achieve their intended utility. The surface of a nanoparticle core material may be modified with one or more surface modifying groups. The surface modifying groups may be derived from various surface modifying agents. Schematically, surface modifying agents may be represented by the following general formula:

$$A-B \quad (II)$$

The A group in Formula II is a linking group that is capable of attaching to the surface of the nanoparticle. In those situations where the nanoparticles and the inactive ingredient or the nanoparticles and the active ingredient are processed in a liquid, the B group is a compatibilizing group with the liquid. The B group may also be a group or moiety that is capable of preventing irreversible agglomeration of the nanoparticles. It is possible for the A and B groups to be the same, e.g., the attaching group may also be capable of providing the desired surface compatibility. The compatibilizing group may be reactive, but is generally non-reactive, with a component of the active or inactive ingredients. The A group may be comprised of more than one component or created in more than one step, e.g., the A group may be comprised of an A' moiety which is reacted with the surface, and an A" moiety which can be reacted with B. The sequence of these reactions is not important, as these reactions can be wholly or partly performed prior to the attachment to the core. Further description of nanoparticles in coatings can be found in Linsenbuhler, M. et. al., *Powder Technology*, 158, 2003, p. 3-20.

Many suitable classes of surface-modifying compounds are known to those skilled in the art and include, for example, silanes, organic acids, organic bases, inorganic acids with organic groups, and alcohols, and combinations thereof. For certain embodiments, including any one of the above embodiments, a surface of the core is modified with a compound selected from the group consisting of alkylsilanes, carboxylic acids, phosphonic acids, sulfonates, polyethylene glycols, sugars, and a combination thereof.

For certain embodiments, the surface-modifying compound is a silane. Examples of silanes include organosilanes such as, for example, alkylchlorosilanes, alkoxysilanes, e.g., methyltrimethoxysilane, methyltriethoxysilane, ethyltrimethoxysilane, ethyltriethoxysilane, n-propyltrimethoxysilane, n-propyltriethoxysilane, isopropyltrimethoxysilane, isopropyltriethoxysilane, butyltrimethoxysilane, butyltriethoxysilane, hexyltrimethoxysilane, octyltrimethoxysilane, 3-mercaptopropyltrimethoxysilane, n-octyltriethoxysilane, phenyltriethoxysilane, polytriethoxysilane, vinyltrimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri(t-butoxy) silane, vinyltris(isobutoxy)silane, vinyltris(isopropenoxy)silane, and vinyltris(2-methoxyethoxy)silane; trialkoxyarylsilanes; isooctyltrimethoxy-silane; N-(3-triethoxysilylpropyl) methoxyethoxyethoxy ethyl carbamate; N-(3-triethoxysilylpropyl) methoxyethoxyethoxyethyl carbamate; silane functional (meth)acrylates including, e.g., 3-(methacryloyloxy)propyltrimethoxysilane, 3-acryloyloxypropyltrimethoxysilane, 3-(methacryloyloxy)propyltriethoxysilane, 3-(methacryloyloxy)propylmethyldimethoxysilane, 3-(acryloyloxypropyl)methyldimethoxysilane, 3-(methacryloyloxy)propyldimethylethoxysilane, 3-(methacryloyloxy)methyltriethoxysilane, 3-(methacryloyloxy)methyltrimethoxysilane, 3-(methacryloyloxy)propyldimethylethoxysilane, 3-(methacryloyloxy) propenyltrimethoxysilane, and 3-(methacryloyloxy) propyltrimethoxysilane; polydialkylsiloxanes including, e.g., polydimethylsiloxane, arylsilanes including, e.g., substituted and unsubstituted arylsilanes, alkylsilanes including, e.g., substituted and unsubstituted alkyl silanes including, e.g., methoxy and hydroxy substituted alkyl silanes, and combinations thereof.

Methods of surface-modifying silica using silane functional (meth)acrylates are known and are described, for example, in U.S. Pat. No. 4,491,508 (Olson et al.); U.S. Pat. No. 4,455,205 (Olson et al.); U.S. Pat. No. 4,478,876 (Chung); U.S. Pat. No. 4,486,504 (Chung); and U.S. Pat. No. 5,258,225 (Katsamberis) whose descriptions are incorporated herein by reference for such purpose. Surface-modified silica nanoparticles include silica nanoparticles surface-modified with silane surface modifying agents including, for example, acryloyloxypropyl trimethoxysilane, 3-methacryloyloxypropyltrimethoxysilane, 3-mercaptopropyltrimethoxysilane, n-octyltrimethoxysilane, isooctyltrimethoxysilane, and combinations thereof. Silica nanoparticles can be treated with a number of surface modifying agents including, for example, an alcohol, an organosilane including, for example, alkyltrichlorosilanes, trialkoxyarylsilanes, trialkoxy(alkyl)silanes, and combinations thereof, and organotitanates, and mixtures thereof.

In another embodiment, the surface-modifying compound is an organic acid or an inorganic acid with an organic group. Examples of such compounds include oxyacids of carbon (e.g., carboxylic acid), sulfur and phosphorus, acid derivatized poly(ethylene glycols) (PEGs) and combinations of any of these. Suitable phosphorus containing acids include phosphonic acids including, for example, octylphosphonic acid, laurylphosphonic acid, decylphosphonic acid, dodecylphosphonic acid, octadecylphosphonic acid, monopolyethylene glycol phosphonate and phosphates including lauryl or stearyl phosphate. Suitable sulfur containing acids include sulfates and sulfonic acids including dodecyl sulfate and lauryl sulfonate. Any such acids may be used in either acid or salt forms.

Other surface modifying compounds with carboxyl groups include acrylic acid, methacrylic acid, beta-carboxyethyl acrylate, mono-2-(methacryloyloxyethyl) succinate, mono(methacryloyloxypolyethyleneglycol) succinate and combinations of one or more of such compounds. For certain embodiments, surface-modifying agents which incorporate a carboxylic acid functionality include, for example, $CH_3O(CH_2CH_2O)_2CH_2COOH$ (hereafter MEEAA), 2-(2-methoxyethoxy)acetic acid having the chemical structure $CH_3OCH_2CH_2OCH_2COOH$ (hereafter MEAA), mono(polyethylene glycol) succinate in either acid or salt form, octanoic acid, dodecanoic acid, steric acid, acrylic and oleic acid or their acidic derivatives. In a further embodiment, surface-modified iron oxide nanoparticles include those modified with endogenous fatty acids, e.g., steric acid, or fatty acid derivatives using endogenous compounds, e.g., steroyl lactylate or sarcosine or taurine derivatives.

In another embodiment, the surface-modifying compound is an organic base. Examples of such compounds include alkylamines, e.g., octylamine, decylamine, dodecylamine, octadecylamine, and monopolyethylene glycol amines.

In another embodiment, the surface-modifying compound is an alcohol or thiol. Examples of such compounds include, for example, aliphatic alcohols, e.g., octadecyl, dodecyl, lauryl and furfuryl alcohol, alicyclic alcohols, e.g., cyclohexanol, and aromatic alcohols, e.g., phenol and benzyl alcohol, and combinations thereof. Thiol-based compounds are especially suitable for modifying cores with gold surfaces.

The surface-modified nanoparticles are selected in such a way that compositions formed with them are free from a degree of particle agglomeration or aggregation that would interfere with the desired properties of the composition. The surface-modified nanoparticles are generally selected to be either hydrophobic or hydrophilic such that, depending on the character of the processing liquid, the active ingredient, or the inactive ingredient, the resulting mixture or blend exhibits substantially free flowing properties. Suitable surface groups constituting the surface modification of the utilized nanoparticles can thus be selected based upon these considerations. When a processing liquid is hydrophobic, for example, one skilled in the art can select from among various hydrophobic surface groups to achieve a surface-modified particle that is compatible with the hydrophobic liquid; when the processing liquid is hydrophilic, one skilled in the art can select from various hydrophilic surface groups; and, when the solvent is a hydrofluorocarbon, one skilled in the art can select from among various compatible surface groups; and so forth. The nanoparticle can include two or more different surface groups (e.g., a combination of hydrophilic and hydrophobic groups) that combine to provide a nanoparticle having a desired set of characteristics. The surface groups will generally be selected to provide a statistically averaged, randomly surface-modified nanoparticle.

The surface groups will be present on the surface of the nanoparticle in an amount sufficient to provide surface-modified nanoparticles with the properties necessary for compatibility with processing liquid, the active ingredient, or the inactive ingredient. In an exemplary embodiment, the surface groups are present in an amount sufficient to form a monolayer, and in another embodiment, a continuous monolayer, on at least a substantial portion of the surface of the nanoparticle.

A variety of methods are available for modifying the surfaces of nanoparticles. A surface modifying agent may, for example, be added to nanoparticles (e.g., in the form of a powder or a colloidal dispersion) and the surface modifying agent may be allowed to react with the nanoparticles. One skilled in the art will recognize that multiple synthetic sequences to bring the nanoparticle together with the compatibilizing group are known and can be used. For example, the reactive group/linker may be reacted with the nanoparticle followed by reaction with the compatibilizing group. Alternatively, the reactive group/linker may be reacted with the compatibilizing group followed by reaction with the nanoparticle. Other surface modification processes are described in, e g., U.S. Pat. No. 2,801,185 (Iler) and U.S. Pat. No. 4,522,958 (Das et al.), whose descriptions are incorporated herein by reference for such purpose.

Surface-modified nanoparticles or precursors to them may be in the form of a colloidal dispersion. Some such dispersions are commercially available as unmodified silica starting materials, for example those nano-sized colloidal silicas available under the product designations NALCO 1040, 1050, 1060, 2326, 2327, and 2329 colloidal silica from Nalco Chemical Co. of Naperville, Ill. Metal oxide colloidal dispersions include colloidal titanium oxide, examples of which are described in U.S. Pat. Nos. 6,329,058 and 6,432,526 (Arney et al.), whose descriptions are also incorporated by reference herein. Such particles are also suitable substrates for further surface modification as described above.

For certain embodiments, including any one of the above embodiments, the surface-modified nanoparticles have a mean particle diameter of not more than 50 nm. For certain of these embodiments, the surface-modified nanoparticles have a mean diameter of not more than 20 nanometers. For certain of these embodiments, the surface-modified nanoparticles have a mean diameter of 2 nm to 20 nm; and in certain other embodiments from 3 nm to 10 nm or more preferably from 4 nm to 8 nm. If the chosen surface-modified nanoparticle or combination of surface-modified nanoparticles are themselves aggregated, the maximum preferred cross-sectional dimension of the aggregated surface-modified nanoparticles will be within any one of these stated ranges.

The surface-modified nanoparticles are present in the dry powder compositions described herein in an amount effective to enhance a property which is relevant to processing or delivering the composition. For example, the degree of aggregation, agglomeration or flocculation of the active ingredient, the inactive ingredient, or both can be reduced or minimized by the surface-modified nanoparticles. The amount of surface-modified nanoparticle effective to achieve such purposes will depend, inter alia, on the composition of the bulk material, the chosen nanoparticle, the presence or absence of other adjuvants or excipients and on the particular needs and requirements of the application for which the active ingredient, the inactive ingredient, or both are to be used. For example, the nature of the nanoparticle surface, the morphology of the particle and particle size may each influence the desired properties of the composition and influence the selection of a nanoparticle and the amount or concentration of nanoparticles used. The presence of as little as 0.0001 percent of nanoparticles by weight of the composition may provide a desired effect. For certain embodiments, the amount of surface-modified nanoparticles is at least 0.01 weight percent. The surface-modified nanoparticles may be used in an amount not exceeding 10 weight percent, and in certain embodiments in an amount not more than 5 weight percent of the composition. For certain embodiments, including any one of the above embodiments, the amount of surface-modified nanoparticles in the composition is at least 0.02 percent and not more than 5 percent by weight of the composition. For certain of these embodiments, the amount of surface-modified nanoparticles in the composition is 0.1 to 3 weight percent of the dry powder composition.

In certain applications it may be preferred that the selected nanoparticles be substantially spherical. The biocompatibility, including toxicology, and physical properties of a selected surface-modified nanoparticle is considered according to the skill in the art for the present dry powder compositions in accordance with the contemplated use or application.

In one exemplary embodiment, the surface-modified nanoparticles will not irreversibly associate with one another. The term "associate with" or "associating with" includes, for example, covalent bonding, hydrogen bonding, electrostatic attraction, London forces, and hydrophobic interactions.

The surface-modified nanoparticles used in the present compositions as described above can in certain embodiments provide a significant increase in delivery efficiency of an active ingredient, a significant increase in respirable fraction, or both. For certain embodiments, including any one of the above embodiments, the composition has a respirable fraction which is at least 20 percent greater than 1) a composition with the same ingredients without nanoparticles and 2) a composition made by adding the nanoparticles to the same ingredients at the same time. For certain of these embodiments, the respirable fraction is at least 30 percent greater. For certain of these embodiments, the respirable fraction is at least 50 percent greater or at least 75 percent greater.

For certain embodiments, including any one of the above embodiments, the composition has an active ingredient delivery efficiency which is at least 10 percent greater than 1) a composition with the same ingredients without nanoparticles and 2) a composition made by adding the nanoparticles to the same ingredients at the same time. For certain of these embodiments, the delivery efficiency is at least 20 percent greater. For certain of these embodiments, the delivery efficiency is at least 50 percent greater.

The surface-modified nanoparticles utilized in the dry powder compositions described herein typically enhance and/or maintain the flowability of the powder composition. Flowability (also called free flow) refers generally to the ability of a free-flowing material to flow steadily and consistently as individual particles or groups of individual particles such as would occur, for example, through a fine orifice. Relative improvements (i.e., reductions) in aggregation, agglomeration, attrition, flocculation, segregation, caking, bridging or in the ability to achieve uniform blends indicate an improvement in flowability.

The presence of nanoparticles in the present compositions can also enhance floodability (also called floodable flow), which refers to the tendency of a solid or powder material toward liquid-like flow due to the material fluidization of a mass of particles by a gaseous carrier.

Also, the presence of the surface-modified nanoparticles may allow for higher tap densities, where a larger concentration of a dry powder composition described herein may be contained in a capsule, a blister, or a reservoir-based DPI device. For example, this may contribute to more doses in a DPI device within the same sized device, rather than changing the device's shape or size.

In another embodiment, the dry powder inhalation device described herein may have the dry powder composition stored in a storage device prior to dosing. This storage device may comprise, for example, a reservoir, capsule, blister, or dimpled tape. In an exemplary embodiment, the micronized active ingredient used in the composition is a micronized crystalline powder, but may also be an amorphous powder from a process such as spray drying. Additionally, the active ingredient may be contained in particles that are a matrix of drug and an excipient. The dry powder inhalation device may be a multi-dose device or may be a single dose device. The dry powder inhalation device may be either a passive device or an active device.

In a further embodiment, the dry powder pharmaceutical composition may be used for delivering medicament to the lungs of a mammal by oral inhalation delivery.

Objects and advantages of this invention are further illustrated by the following examples, but the particular materials and amounts thereof recited in these examples, as well as other conditions and details, should not be construed to limit the scope of the present invention.

EXAMPLES

Unless otherwise indicated, all parts and percentages are by weight.

Aerosol Performance Test Methods

The ability of the powder to be aerosolized was measured using an inertial cascade impactor as follows. A small amount (nominally 4 mg) of powder was weighed into a size three Shionogi QUALI-V hydroxypropyl methylcellulose capsule (Shionogi Qualicaps, Madrid, Spain) and loaded into an AEROLIZER device ("DPI" device, commercially available as a FORADIL AEROLIZER product, available from Schering Plough Co.), which was tested for pharmaceutical performance using a Next Generation Pharmaceutical Impactor ("NGI") (MSP Corporation, Shoreview, Minn.). For examples 1 through 5 and comparative examples 1 and 2 the NGI was additionally fitted with a preseparator (MSP Corporation, Shoreview, Minn.). A series of diluted formulations having a nominal concentration of 5 weight % budesonide, blended with a large particle size lactose as a bulking agent, were tested for performance. The formulations differed by the amount and type of surface-modified nanoparticles and/or the way in which the surface-modified nanoparticles were added to the formulation. At a 5% budesonide concentration, the 4 mg dose size used for testing provided an effective dose of 200 µg. Comparator formulations consisting of a simple blend of untreated budesonide with the large particle size lactose, and the same blend treated with surface-modified nanoparticles by dispersing and mixing all three components in solvent, were also tested. The NGI was coupled with a USP throat (United States Pharmacopeia, USP 24 <601> Aerosols, Metered Dose Inhalers, and Dry Powder Inhalers) and operated at a standard flow rate of 60 Lpm for a collection time of four seconds. A suitable coupler was affixed to the USP throat to provide an air-tight seal between the DPI device and the throat. For all testing, the USP throat and stage cups 4-7 of the NGI were coated with a surfactant, a 10 mL aliquot of diluent was placed in the preseparator, and a 3 mL aliquot of diluent was placed in stage cups 1-3 of the NGI to prevent particle bounce and re-entrainment. The amount of drug collected on each component of the NGI testing apparatus was determined by rinsing the component with a measured volume of an appropriate solvent and subjecting the rinsed material to HPLC analysis with ultraviolet detection to determine drug concentration. Data that was returned from HPLC analysis was analyzed to determine the average amount of drug collected on the DPI and capsule, the USP throat, and on each component of the NGI per delivered dose.

Using the individual component values, the respirable fraction and delivery efficiency were calculated for each powder sample. Respirable mass was defined as the total delivered dose that was measured to be smaller than the respirable limit of 4.5 micrometers in aerodynamic diameter. Respirable fraction was defined as the percentage of a delivered dose that reached the entry of the throat and was smaller than the respirable limit. Delivery efficiency was defined as the respirable mass divided by the total delivered dose. When using the NGI, respirable mass was collected in cups 3, 4, 5, 6, and 7, and on the filter. Mass collected in the throat, preseparator, and cups 1 and 2 were considered non-respirable.

Example 1

Hydrophobic silica surface-modified nanoparticles (SMN) were prepared by mixing 600 grams of Nalco 2326 colloidal silica, 56.8 grams of isooctyltrimethoxysilane (Gelest, Inc.), 540 grams of ethanol, and 135 grams of methanol in a 2 liter flask at approximately 82° C. for 4 hours. The resulting white particulate product was isolated and oven dried at 120° C.

A surface-modified nanoparticle dispersion was prepared by adding 5.0028 grams of the hydrophobic silica SMN to 500 mL of heptane and stirring until the SMN had completely dispersed. The resulting SMN-heptane dispersion had a nominal concentration of 0.010 g/mL. Lactose (IN-HALAC 230, lactose monohydrate, approximate particle sizes: d10=60 µm, d50=100 µm, d90=140 µm, available from Meggle GmbH, Wasserburg, Germany) (20.0118 grams) was added to a 500 mL round bottom flask. An aliquot of 41 mL of the SMN-heptane dispersion was added to the flask along with an additional 50 mL of heptane. The mixture was then sonicated for approximately 15 seconds to ensure uniform mixture in the flask. The flask was then placed onto a rotary evaporator to remove the solvent. The rotary evaporator was set to a nominal temperature of 60° C. and operated under a vacuum. After removal of all of the visible solvent, the flask was then placed into a vacuum oven at approximately 45° C. for approximately 1 hour to remove further residual solvent. The resulting powder was sieved with a No. 70 mesh sieve (210 micron openings) to break up any agglomerated material. The sieved material was then collected and placed in a container for later use. The lactose-SMN powder blend had a nominal concentration of surface-modified nanoparticles of 2.0 percent by weight of the powder blend (% w/w).

Micronized budesonide (approximate particle sizes: d10=1.116 µm, d50=1.878 µm, d90=3.200 µm, available from Onbio Inc., Ontario, Canada) (0.1597 grams) and 3.0067 grams of the lactose-SMN powder blend were added to a 4 inch by 4 inch (10 cm×10 cm) plastic bag with a ZIPLOCK seal. The contents of the bag were mixed first by gently kneading the contents of the bag followed by shaking the contents of the bag. This cycle of kneading-shaking was repeated approximately five times during a total mixing time of approximately three minutes. The contents of the bag were then transferred into a 20 mL glass vial. Care was taken to minimize the amount of residual powder left in the bag. The powder transferred to the vial was then further mixed on a vortex mixer for approximately 15 sec. The resulting budesonide-lactose-SMN powder blend had a nominal budesonide concentration of 5.0% w/w and a nominal SMN concentration of 2.0% w/w. Aerosol performance testing as described in the section above was performed, and the resulting respirable fraction was 53%, and the delivery efficiency was 33%.

Example 2

A lactose-SMN powder blend was prepared as in Example 1 with the exception that the nominal concentration of surface-modified nanoparticles was adjusted to be 0.5% w/w. This powder was blended with micronized budesonide as in Example 1 to prepare a powder blend having a nominal budesonide concentration of 5.0% w/w and a nominal SMN concentration of 0.5% w/w. Aerosol performance testing as described in the section above was performed, and the resulting respirable fraction was 63%, and the delivery efficiency was 43%.

Example 3

A surface-modified nanoparticle dispersion was prepared by adding 5.0028 grams of hydrophobic silica SMN prepared as described in Example 1 to 500 mL of heptane and stirring until the SMN had completely dispersed. The resulting SMN-heptane dispersion had a nominal concentration of 0.010 g/mL. Budesonide (approximate particle sizes: d10=1.116 µm, d50=1.878 µm, d90=3.200 µm, available from Onbio Inc., Ontario, Canada) (10.0131 grams) was added to a 250 mL round bottom flask. An aliquot of 21 mL of the SMN-heptane dispersion was added to the flask along with an additional 60 mL of heptane. The mixture was then sonicated for approximately 30 seconds to ensure uniform mixture in the flask. The flask was then placed onto a rotary evaporator to remove the solvent. The rotary evaporator was set to a nominal temperature of 60° C. and operated under a vacuum. After removal of all of the visible solvent, the flask was then placed into a vacuum oven at approximately 45° C. for approximately 1 hour to remove further residual solvent. The resulting powder was sieved with a No. 140 mesh sieve (106 micron openings) to break up any agglomerated material. The sieved material was then collected and placed in a container for later use. The budesonide-SMN powder blend had a nominal concentration of surface-modified nanoparticles of 2.0% w/w. A lactose-SMN powder blend with a nominal concentration of surface-modified nanoparticles of 2.0% w/w was prepared as in Example 1.

Budesonide-SMN powder blend (0.1609 grams) and 3.0046 grams of the lactose-SMN powder blend were added to a 4 inch by 4 inch (10 cm×10 cm) plastic bag with a ziplock seal. The contents of the bag were mixed first by gently kneading the contents of the bag followed by shaking the contents of the bag. This cycle of kneading-shaking was repeated approximately five times during a total mixing time of approximately three minutes. The contents of the bag were then transferred into a 20 mL glass vial. Care was taken to minimize the amount of residual powder left in the bag. The powder transferred to the vial was then further mixed on a vortex mixer for approximately 15 sec. This blend had a nominal budesonide concentration of 5.0% w/w and a nominal SMN concentration of 2.0% w/w. Aerosol performance testing as described in the section above was performed, and the resulting respirable fraction was 72%, and the delivery efficiency was 44%.

Example 4

A lactose-SMN powder blend with a nominal concentration of surface-modified nanoparticles of 0.5% w/w was prepared was prepared as in Example 2. A budesonide-SMN powder blend with a nominal concentration of surface-modified nanoparticles of 2.0% w/w was prepared as in Example 3.

Budesonide-SMN powder blend (0.1602 grams) and 3.0029 grams of the lactose-SMN powder blend were added to a 4 inch by 4 inch (10 cm×10 cm) plastic bag with a ZIPLOCK seal. The contents of the bag were mixed first by gently kneading the contents of the bag followed by shaking the contents of the bag. This cycle of kneading-shaking was repeated approximately five times during a total mixing time of approximately three minutes. The contents of the bag were then transferred into a 20 mL glass vial. Care was taken to minimize the amount of residual powder left in the bag. The powder transferred to the vial was then further mixed on a vortex mixer for approximately 15 sec. This blend had a nominal budesonide concentration of 5.0% w/w and a nominal SMN concentration of 0.5% w/w. Aerosol performance testing as described in the section above was performed, and the resulting respirable fraction was 63%, and the delivery efficiency was 43%.

Example 5

A budesonide-SMN powder blend with a nominal concentration of surface-modified nanoparticles of 2.0% w/w was prepared as in Example 3. Budesonide-SMN powder blend (0.1607 grams) and 3.0107 grams of lactose (INHALAC 230, lactose monohydrate, approximate particle sizes: d10=60 µm, d50=100 µm, d90=140 µm, available from Meggle GmbH, Wasserburg, Germany) were added to a 4 inch by 4 inch (10 cm×10 cm) plastic bag with a ZIPLOCK seal. The contents of the bag were mixed first by gently kneading the contents of the bag followed by shaking the contents of the bag. This cycle of kneading-shaking was repeated approximately five times during a total mixing time of approximately three minutes. The contents of the bag were then transferred into a 20 mL glass vial. Care was taken to minimize the amount of residual powder left in the bag. The powder transferred to the vial was then further mixed on a vortex mixer for approximately 15 sec. This blend had a nominal budesonide concentration of 5.0% and a nominal SMN concentration of 0.1% w/w. Aerosol performance testing as described in the section above was performed, and the resulting respirable fraction was 44%, and the delivery efficiency was 31%.

Comparative Example 1

Micronized budesonide (approximate particle sizes: d10=1.116 µm, d50=1.878 µm, d90=3.200 µm, available from Onbio Inc., Ontario, Canada) (0.1597 grams) and 3.0040 grams of lactose (INHALAC 230, lactose monohydrate, approximate particle sizes: d10=60 µm, d50=100 µm, d90=140 µm, available from Meggle GmbH, Wasserburg, Germany) were added to a 4 inch by 4 inch (10 cm×10 cm) plastic bag with a ZIPLOCK seal. The contents of the bag were mixed first by gently kneading the contents of the bag followed by shaking the contents of the bag. This cycle of kneading-shaking was repeated approximately five times during a total mixing time of approximately three minutes. The contents of the bag were then transferred into a 20 mL glass vial. Care was taken to minimize the amount of residual powder left in the bag. The powder transferred to the vial was then further mixed on a vortex mixer for approximately 15 sec. This blend had a nominal budesonide concentration of 5.0% w/w. Aerosol performance testing as described in the section above was performed, and the resulting respirable fraction was 33%, and the delivery efficiency was 27%.

Comparative Example 2

A surface-modified nanoparticle dispersion was prepared by adding 5.0028 grams of hydrophobic silica SMN prepared as described in Example 1 to 500 mL of heptane and stirring until the SMN had completely dispersed. The resulting SMN-heptane dispersion had a nominal concentration of 0.010 g/mL. Budesonide (approximate particle sizes: d10=1.116 µm, d50=1.878 µm, d90=3.200 µm, available from Onbio Inc., Ontario, Canada) (0.2646 grams) was added to a 50 mL beaker. Approximately 10 mL heptane was added to the beaker to wet the budesonide. An aliquot of 3 mL of the SMN-heptane dispersion was added to the beaker. The budesonide-SMN-heptane mixture was then sonicated for approximately 5 seconds to ensure uniform mixture in the beaker.

Lactose (INHALAC 230, lactose monohydrate, approximate particle sizes: d10=60 µm, d50=100 µm, d90=140 µm, available from Meggle GmbH, Wasserburg, Germany) (5.0327 grams) was added to a 250 mL round bottom flask. An aliquot of 8 mL of the SMN-heptane dispersion was added to the flask along with an additional 30 mL of heptane. The mixture was then sonicated for approximately 5 seconds to ensure uniform mixture in the flask.

The budesonide-SMN-heptane mixture was then added to the 250 mL round bottom flask along with an additional 30 mL of heptane. The resulting SMN-budesonide-lactose-heptane dispersion was then sonicated for approximately 20 seconds to ensure uniform mixture in the flask. The flask was then placed onto a rotary evaporator to remove the solvent. The rotary evaporator was set to a nominal temperature of 60° C. and operated under a vacuum. After removal of all of the visible solvent, the flask was then placed into a vacuum oven at approximately 45° C. for approximately 1 hour to remove further residual solvent. The resulting powder was sieved with a No. 70 mesh sieve (210 micron openings) to break up any agglomerated material. The sieved material was then collected and placed in a container for later use. The dried lactose-budesonide-SMN powder blend had a nominal budesonide concentration of 5.0% w/w and a nominal concentration of surface-modified nanoparticles of 2.0% w/w. Aerosol performance testing as described in the section above was performed, and the resulting respirable fraction was 35%, and the delivery efficiency was 25%.

Example 6

Hydrophobic calcium phosphate surface-modified nanoparticles (SMN) were prepared by mixing 25 grams of calcium chloride hexahydrate (Fluka) and 80.25 grams of isooctyltrimethoxysilane (Gelest, Inc.) in a 0.5 liter flask at approximately 110° C. under a stream of nitrogen until phase separation was observed, then adding a solution of phosphoric acid (11.18 grams in 5 grams of methanol with 80.65 grams trioctylamine (Alfa Aesar)). Heptane (100 mL) was then added to the reaction mixture, which was held at 110° C. for an additional two hours. The heptane was removed via a Dean-Stark collector, and the hot reaction mixture was poured into a 1 liter flask containing 800 mL of methanol, resulting in precipitation of a white solid. The solid was isolated by decanting the liquid, and was then washed by adding an ethanol/methanol mixture and stirring overnight, followed by centrifugation to isolate the solid. The solid was then dried in a 110° C. oven for one hour. The dried solid was redispersed in hexanes and centrifuged, which was then washed a second time by adding to 400 mL of ethanol and stirring overnight. The solids were isolated by centrifugation and decantation of the supernatant, and were then dried in a 110° C. oven for two hours. The solid was then washed a third time by adding ethanol and stirring overnight. The solids were isolated by centrifugation and decantation of the supernatant, and were then dried in a 110° C. oven for two hours.

A surface-modified nanoparticle dispersion was prepared by adding 1.0002 grams of the hydrophobic calcium phosphate SMN to 200 mL of heptane and sonicating until the SMN had completely dispersed. The resulting SMN-heptane dispersion had a nominal concentration of 0.005 g/mL. Lactose (INHALAC 250, lactose monohydrate, approximate particle sizes: d10=20 µm, d50=55 µm, d90=95 µm, available from Meggle GmbH, Wasserburg, Germany) (49.868 grams) was added to a 500 mL round bottom flask. An aliquot of 25 mL of the SMN-heptane dispersion was added to the flask along with an additional 200 mL of heptane. The mixture was then sonicated briefly to ensure uniform mixture in the flask. The flask was then placed onto a rotary evaporator to remove the solvent. The rotary evaporator was set to a nominal temperature of 50° C. and operated under a vacuum. After removal of all of the visible solvent, the flask was then placed into a DESPATCH oven at approximately 120° C. for approximately 1 hour to remove further residual solvent. The resulting powder was sieved with a No. 60 mesh sieve (250 micron openings) to break up any agglomerated material. The sieved material was then collected and placed in a container for later use. The lactose-SMN powder blend had a nominal concentration of surface-modified nanoparticles of 0.25 percent by weight of the powder blend (% w/w).

Micronized budesonide (approximate particle sizes: d10=1.116 µm, d50=1.878 µm, d90=3.200 µm, available from Onbio Inc., Ontario, Canada) (0.2496 grams) and 4.7503 grams of the lactose-SMN powder blend were added to a 20 mL glass vial. The contents of the vial were mixed on a vortex mixer for approximately 3 minutes at setting 8. This blend had a nominal budesonide concentration of 5.0% w/w and a nominal SMN concentration of 0.25% w/w. Aerosol performance testing as described in the section above was performed, and the resulting respirable fraction was 39%, and the delivery efficiency was 24%.

Example 7

A lactose-SMN powder blend was prepared as in Example 6 with the exception that the nominal concentration of surface-modified nanoparticles was adjusted to be 0.5% w/w. This powder was blended with micronized budesonide as in Example 6 to prepare a powder blend having a nominal budesonide concentration of 5.0% w/w and a nominal SMN concentration of 0.5% w/w. Aerosol performance testing as described in the section above was performed, and the resulting respirable fraction was 38%, and the delivery efficiency was 43%.

Example 8

A surface-modified nanoparticle dispersion was prepared by adding 2.0002 grams of the hydrophobic calcium phosphate SMN to 200 mL of heptane and sonicating until the SMN had completely dispersed. The resulting SMN-heptane dispersion had a nominal concentration of 0.0100 g/mL. Lactose (INHALAC 250, lactose monohydrate, approximate particle sizes: d10=20 µm, d50=55 µm, d90=95 µm, available from Meggle GmbH, Wasserburg, Germany) (49.495 grams) was added to a 500 mL round bottom flask. An aliquot of 50 mL of the SMN-heptane dispersion was added to the flask along with an additional 200 mL of heptane. The mixture was then sonicated briefly to ensure uniform mixture in the flask. The flask was then placed onto a rotary evaporator to remove the solvent. The rotary evaporator was set to a nominal temperature of 50° C. and operated under a vacuum. After removal of all of the visible solvent, the flask was then placed into a Despatch oven at approximately 120° C. for approximately 1 hour to remove further residual solvent. The resulting powder was sieved with a No. 60 mesh sieve (250 micron openings) to break up any agglomerated material. The sieved material was then collected and placed in a container for later use. The lactose-SMN powder blend had a nominal concentration of surface-modified nanoparticles of 1.0 percent by weight of the powder blend (% w/w).

This powder was blended with micronized budesonide as in Example 6 to prepare a powder blend having a nominal budesonide concentration of 5.0% w/w and a nominal SMN concentration of 1.0% w/w. Aerosol performance testing as described in the section above was performed, and the resulting respirable fraction was 42%, and the delivery efficiency was 26%.

Comparative Example 3

Micronized budesonide (approximate particle sizes: d10=1.116 µm, d50=1.878 µm, d90=3.200 µm, available from Onbio Inc., Ontario, Canada) (0.2503 grams) and 4.7482 grams of lactose (INHALAC 250, lactose monohydrate, approximate particle sizes: d10=20 µm, d50=55 µm, d90=95 µm, available from Meggle GmbH, Wasserburg, Germany) were added to a 20 mL glass vial. The contents of the vial were mixed on a vortex mixer for approximately 3 minutes at setting 8. This blend had a nominal budesonide concentration of 5.0% w/w. Aerosol performance testing as described in the section above was performed, and the resulting respirable fraction was 29%, and the delivery efficiency was 16%.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

The complete disclosures of the patents, patent documents, and publications cited herein are incorporated by reference in their entirety or the portions of each that are indicated as if each were individually incorporated.

What is claimed is:

1. A method of making a dry powder pharmaceutical composition comprising:
   providing an inactive ingredient comprising particles;
   providing a micronized active ingredient; and
   mixing surface-modified nanoparticles with the inactive ingredient particles and, separately, mixing surface-modified nanoparticles with the micronized active ingredient;
   wherein mixing the surface-modified nanoparticles with the inactive ingredient particles provides an inactive ingredient comprising particles having surfaces with the surface-modified nanoparticles deposited on the surfaces, wherein mixing the inactive ingredient particles with the surface-modified nanoparticles is carried out in a liquid, and then the liquid is removed, and wherein the inactive ingredient particles are insoluble in the liquid, and the surface-modified nanoparticles are dispersible in the liquid; and
   wherein mixing the surface-modified nanoparticles with the micronized active ingredient provides a micronized active ingredient comprising particles having surfaces with the surface-modified nanoparticles deposited on the surfaces, wherein mixing the micronized active ingredient with the surface-modified nanoparticles is carried out in a liquid, and then the liquid is removed, and wherein the micronized active ingredient is insoluble in the liquid, and the surface-modified nanoparticles are dispersible in the liquid; and
   then mixing the micronized active ingredient comprising particles having surfaces with the surface-modified nanoparticles deposited on the surfaces with the inactive ingredient comprising particles having surfaces with the surface-modified nanoparticles deposited on the surfaces.

2. The method of making a composition of claim 1, wherein the liquid is removed by spray drying, rotary evaporation, bulk evaporation, or freeze drying.

3. The method of making a composition of claim 1, wherein the inactive ingredient is comprised of particles having a mean physical diameter of less than 200 micrometers.

4. The method of making a composition of claim 1, wherein the active ingredient is comprised of particles having a mean aerodynamic diameter of less than 5 micrometers.

5. The method of making a composition of claim 1, wherein the mean physical diameter of the particles comprising the inactive ingredient is at least 10 fold greater than the mean aerodynamic diameter of the particles comprising the active ingredient.

6. The method of making a composition of claim 1, wherein the active ingredient and the inactive ingredient are each present in an amount such that the weight ratio of the amount of active ingredient to the amount of the inactive ingredient is not more than 1:3.

7. The method of making a composition of claim 1, wherein the inactive ingredient is selected from the group consisting of lactose, trehalose, sucrose, mannitol, or a combination thereof.

8. The method of making a composition of claim 1, wherein the active ingredient is selected from the group consisting of antiallergics, antiasthmatics, antiinflammatories, bronchodilators, steroids, anticholinergics, salts thereof, solvates thereof, enantiomers thereof, and a combination thereof.

9. The method of making a composition of claim 8, wherein the active ingredient is selected from the group consisting of budesonide, albuterol, formoterol, fluticasone, salmeterol, mometasone, tiotropium, beclomethasone, salts thereof, solvates thereof, enantiomers thereof, and a combination thereof.

10. The method of making a composition of claim 1, wherein the surface-modified nanoparticles comprise a core, the core comprising an inorganic material selected from the group consisting of silica, titania, alumina, an oxide of zinc, an oxide of iron, metal phosphates, metal sulfates, metal chlorides, and a combination thereof.

11. The method of making a composition of claim 1, wherein the surface-modified nanoparticles comprise a core, the core comprising an organic polymer.

12. The method of making a composition of claim 1, wherein the nanoparticles have a mean diameter of not more than 20 nanometers.

13. The method of making a composition of claim 1, wherein the amount of surface-modified nanoparticles in the composition is at least 0.02 percent and not more than 5 percent by weight of the composition.

14. The method of making a composition of claim 1, wherein the composition has a respirable fraction which is at least 20 percent greater than a composition with the same ingredients without nanoparticles and a composition made by adding the nanoparticles to the same ingredients at the same time.

15. The method of making a composition of claim 1, wherein the composition has an active ingredient delivery efficiency which is at least 10 percent greater than a composition with the same ingredients without nanoparticles and a composition made by adding the nanoparticles to the same ingredients at the same time.

* * * * *